(12) United States Patent
Larsson et al.

(10) Patent No.: US 7,348,358 B2
(45) Date of Patent: Mar. 25, 2008

(54) USE OF CYCLOLIGNANS

(75) Inventors: Olle Larsson, Taby (SE); Magnus Axelson, Hasselby (SE)

(73) Assignee: Axelar AB, Stockholm (SE)

( * ) Notice: Subject to any disclaimer, the term of this patent is extended or adjusted under 35 U.S.C. 154(b) by 258 days.

(21) Appl. No.: 10/481,441

(22) PCT Filed: Jun. 19, 2002

(86) PCT No.: PCT/SE02/01202

§ 371 (c)(1),
(2), (4) Date: Dec. 19, 2003

(87) PCT Pub. No.: WO02/102804

PCT Pub. Date: Dec. 27, 2002

(65) Prior Publication Data

US 2004/0186169 A1    Sep. 23, 2004

(30) Foreign Application Priority Data

Jun. 19, 2001   (SE)   .................................... 0102168

(51) Int. Cl.
*A01K 31/335* (2006.01)
*C07D 317/70* (2006.01)
*C07D 307/77* (2006.01)

(52) U.S. Cl. ........................ 514/463; 549/298; 549/433
(58) Field of Classification Search ................ 549/298, 549/433; 514/463
See application file for complete search history.

(56) References Cited

U.S. PATENT DOCUMENTS

2004/0186169 A1    9/2004 Larsson et al.

FOREIGN PATENT DOCUMENTS

| EP | 0 188 248 | 7/1986 |
|---|---|---|
| EP | 0188248 | 7/1986 |
| WO | 8604062 | 7/1986 |
| WO | 9928347 | 6/1999 |
| WO | WO 99/28347 | 6/1999 |
| WO | 0152826 | 7/2001 |
| WO | WO 01/52826 | 7/2001 |
| WO | WO 2004093781 A2 * | 11/2004 |

OTHER PUBLICATIONS

U.S. Appl. No. 11/346,294, filed Feb. 3, 2006, Larsson, et al.
U.S. Appl. No. 10/554,399, filed Oct. 24, 2005, Axelson, et al.
International Preliminary Examination Report, Sep. 22, 2003.
European Office Action, Mar. 29, 2004.
European Office Action, Jul. 15, 2004.
European Office Action, Feb. 15, 2005.
M. Novelo, et al., "Cytotoxic Constituents From Hyptis Verticillata[1]", Journal of Natural Products, vol. 56, No. 10, pp. 1728-1736, Oct. 1999.

M. Gordaliza, et al., "Antineoplastic and Antiviral of Podophyllotoxin Related Lignans", Arch. Pharm. (Weinheim), vol. 327, No. 3, pp. 175-179, 1994.
J. Miguel del Corral, et al., "Methyl Ethers of Podophyllotoxin-Rleated Cycolignans", Journal of Natural Products, vol. 58, No. 6, pp. 870-877, Jun. 1995.
O. Buchardt, et al., "Thermal Chemistry of Podophyllotoxin in Ethanol and a Comparison of the Cytostatic Activity of the Thermolysis Products", Journal of Pharmaceutical Sciences, vol. 75, No. 11, Nov. 1986, pp. 1076-1080.
A. San Feliciano, et al., "Antineoplastic and Antiviral Activities of Some Cyclolignans", Plantya Med., vol. 59,, No. 3, 1993, pp. 246-249.
M. Gordaliza, et al., "Synthesis and Antineoplastic Activity of Cyclolignan Aldehydes", Eur. J. Med. Chem., vol. 35, Nos. 7 & 8, 2000, pp. 691-698.
M. Gordaliza, et al., "Immunosuppressive Cyclolignans", J. Med. Chem., 1996, vol. 39, No. 14, pp. 2865-2868.
S. Shashikanth, et al., "Synthesis of Podophyllotoxin and Related Analogs: Part IX. Synthesis of Ethylenedioxy and Indan Analogs of Picropodophyllone and Their Antimitotic Activity", STN International, File CAPLUS, CAPLUS Accession No. 1996:304556, 1996, vol. 5, No. 3, pp. 185-188.
M. Gordaliza, et al., "Cytotoxic Cyclolignans Related to Podophyllotoxin", IL Farmaco, vol. 56, No. 4, Apr. 1, 2001, pp. 297-304.
M. Gordalilza, et al., "Antitumor Properties of Podophyllotoxin and Related Compounds", Current Pharmaceutical Design, 2000, vol. 6, pp. 1811-1839.
A. Girnita, et al., "Cyclolignans as Inhibitors of the Insulin-Like Growth Factor-1 Receptor and Malignant Cell Growth", Cancer Research, vol. 64, pp. 236-242, Jan. 1, 2004.
Miriam Novelo et al.: "Cytotoxic constituents from hyptis verticillata" Journal of Natural Products, vol. 56, No. 10, pp. 1728-1736 Oct. 1993.
Marina Gordaliza et al.: "Antineoplastic and antiviral activiral activities of podophyllotoxin related lignans" Arch. Pharm. (WEINSHEIM), vol. 327, No. 3, 175-179 1994.
J.M. Miguel Del Corral et al.: "Methyl ethers of podophyllotoxin-related cycolignans" Journal of Natural Products, vol. 58, No. 6, pp. 870-877 Jun. 1995.
Ole Buchardt et al.: "Thermal chemistry of podophyllotoxin in ethanol and a comparison of the cytostatic activity of the thermolysis products" Journal of Pharmaceutical Sciences, vol. 75, No. 11, pp. 1076-1080, Nov. 1986.
A. San Feliciano et al.: "Antineoplastic and antiviral activities of some cyclolignans" Planta Medica, vol. 59, No. 3, pp. 246-249 1993.

(Continued)

*Primary Examiner*—Janet L. Andres
*Assistant Examiner*—Raymond Covington
(74) *Attorney, Agent, or Firm*—Oblon, Spivak, McClelland, Maier & Neustadt, P.C.

(57) ABSTRACT

The invention refers to the use of specific cyclolignans, wherein the carbon atoms in positions 9 and 9' have cis configuration, for inhibition of the insulin-like growth factor-1 receptor. Said compounds can be used for treatment of IGF-1R dependent diseases, such as cancer, psoriasis, artherosclerosis and acromegaly. A preferred compound is picropodophyllin.

12 Claims, 8 Drawing Sheets

OTHER PUBLICATIONS

Marina Gordaliza et al.: "Synthesis and antineoplastic activity of cyclolignan aldehydes" Eur. J. Med. Chem., vol. 35, No. 7 & 8, pp. 691-698 2000.

Marina Gordaliza et al.: "Immunosuppressive cyclolignans" J. Med. Chem., vol. 39, No. 14, pp. 2865-2868 1996.

STN International, File CAPLUS, CAPLUS accession No. 1996:304556, document No. 125:10458 S. Shashikanth et al.: "Synthesis of podophyllotoxin and related analogues: part IX. Synthesis of ethylenedioxy and Indan analogues of picropodophyllone and their antimitotic activity" & Indian Journal of Heterocyclic Chemistry (1996), 5(3), 185-188.

Marina Gordaliza et al.: "Cytotoxic cyclolignans related to podophyllotoxin" Il Farmaco, vol. 56, No. 4, pp. 297-304 Apr. 1, 2001.

First Office Action from The Patent Office of the People's Republic of China, issued Mar. 3, 2006.

Foreign Medicine, Physiology, Pathology Science and Clinical Fasciule, 19(6), 1999, pp. 441-443. (*w/English Translation of Related Parts of the Reference Document*).

Journal of China University of Science and Technology, vol. 27, No. 1, Mar. 1997, pp. 113-116. (*w/English Translation of Related Parts of the Reference Document*).

Chemistry Journal of Universities, vol. 18, No. 7, Jul. 1997, pp. 1061-1066. (*w/English Translation of Related Parts of the Reference Document*).

A. Gimita, et al., "The Insulin-Like Growth Factor-1 Receptor Inhibitor Picropodophyllin Causes Tumor Regresion and Attenuates Mechanism (nvolved In Invasion of Uveal Melanoma Cells", Cancer Therapy: Preclinical, vol. 12, No. 4, Feb. 15, 2006, pp. 1383-1391.

E. Menu, et al.. "Inhibiting the IGF-1 Receptor Tyrosine Kinase With The Cyclolignan PPP: An In Vitro And In Vivo In The 5T33MM Mouse Model", Blood, vol. 17, No. 2, Jan. 15, 2006, pp. 655-660.

A. Gimita, et al., "Cyclolignans as Inhibitors of the Insulin-Like Growth Factor-1 Receptor and Malignant Cell Growth", Cancer Research, vol. 64, Jan. 1, 2004, pp. 236-242.

\* cited by examiner

Picropodophyllin

Podophyllotoxin

Deoxypicropodophyllin

β-apopicropodophyllin

USE OF CYCLOLIGNANS

CONTINUING APPLICATION INFORMATION

This application is a national stage of international application No. PCT/SE02/01201, filed on June 19, 2002. This application claims benefit of the filing date of U.S. provisional application Ser. No. 60/300,431, filed on Jun. 26, 2001.

The present invention refers to the use of specific cyclolignans inhibiting the insulin-like growth factor-1 receptor, the IGF-1R, for treatment of IGF-1R dependent diseases, especially cancer.

BACKGROUND OF THE INVENTION

The insulin-like growth factor-1 receptor (IGF-1R) plays an important role in proliferation, protection against apoptosis and transformation of malignant cells. The IGF-1R is also important for maintaining the malignant phenotype of tumour cells, and is involved in tumour cell protection against anti-tumour therapy. In contrast, the IGF-1R does not seem to be an absolute requirement for normal cell growth.

The IGF-1R consists of two identical extracellular α-subunits that are responsible for ligand binding, and two identical β-subunits with transmembrane domain and an intracellular tyrosine kinase domain. The ligand-receptor interaction results in phosphorylation of tyrosine residues in the tyrosine kinase domain, which spans from amino acid 973 to 1229, of the β-subunit. The major sites for phosphorylation are the clustered tyrosines at position 1131, 1135 and 1136 (LeRoith, D., et al., *Endocr Rev* 1995 April; 16(2), 143-63). After autophosphorylation the receptor kinase phosphorylates intracellular proteins, like insulin receptor substrate-1 and Shc, which activate the phosphatidyl inositol-3 kinase and the mitogen-activated protein kinase signalling pathways, respectively.

Based on the pivotal role of IGF-1R in malignant cells, it becomes more and more evident that IGF-1R is a target for cancer therapy (Baserga, R., et al., *Endocrine* Vol. 7, no. 1, 99-102, August 1997). One strategy to interfere with IGF-1R activity is to induce selective inhibition of the IGF-1R tyrosine kinase. However, there are today no available selective inhibitors of IGF-1R.

Drugs containing the notoriously toxic cyclolignan podophyllotoxin have been used for centuries, and its anti-cancer properties have attracted particular interest. Undesired side effects of podophyllotoxin have, however, prevented its use as an anti-cancer drug. The mechanism for the cytotoxicity of podophyllotoxin has been attributed to its binding to β-tubulin, leading to inhibition of microtubule assembly and mitotic arrest. The trans conformation in the lactone ring of podophyllotoxin has been shown to be required for binding to β-tubulin. In contrast, its stereoisomer picropodophyllotoxin, which has a cis configuration in the lactone ring, has a 50-fold lower inhibitory effect on microtubule polymerisation and a more than 35-fold higher LD50 in rats. Because of the low anti-microtubule effect of picropodophyllotoxin this compound has attracted little interest. During the last decades the major interest on podophyllotoxin derivatives has concerned etoposide, which is an ethylidene glucoside derivative of 4'-demethyl-epi-podophyllotoxin. Etoposide, which has no effect on microtubules, is a topoisomerase II inhibitor, and is currently being used as such in cancer therapy.

PRIOR ART

A number of synthetic tyrosine kinase inhibitors, that is tyrphostins, have been studied by Párrizas, M., et al., *Endocrinology* 1997, Vol. 138, No. 4, 1427-1433. The IGF-1R is a member of the tyrosine kinase receptor family, which also includes the receptors of insulin, epidermal growth factor (EGF), nerve growth factor (NGF), and platelet-derived growth factor (PDGF). All of the tyrphostins active on IGF-1R cross-react with the insulin receptor, although two of them showed a moderate preference for IGF-1R. It was therefore suggested that it could be possible to design and synthesize small molecules capable of discriminating between them.

Substrate competitive inhibitors of IGF-1 receptor kinase are discussed by Blum, G., et al. in *Biochemistry* 2000, 39, 15705-15712. A number of lead compounds for inhibitors of the isolated IGF-1R kinase are reported. The search for these compounds was aided by the knowledge of the three-dimensional structure of the insulin receptor kinase domain, which is 84% homologous to the IGF-1R kinase domain. The most potent inhibitor found was tyrphostin AG 538, with an IC50 of 400 nM. However, said inhibitor also blocked the insulin receptor kinase.

Kanter-Lewensohn, L., et al., *Mol Cell Endocr* 165 (2000), 131-137, investigated whether the cytotoxic effect of tamoxifen (TAM) on melanoma cells could depend on interference with the expression or function of the insulin-like growth factor-1 receptor. It was found that, although TAM did not have a strong effect on IGF-1 binding and the expression of IGF-1R at the cell surface, TAM efficiently blocked tyrosine phosphorylation of the IGF-1R β-subunit.

The Chemistry of Podophyllum by J. L. Hartwell et al., Fortschritte der Chemie organischer Naturstoffe 15, 1958, 83-166, gives an overview of podophyllotoxin and different derivatives thereof, commercially derived from two species of plants, Podophyllum peltatum and Podophyllum emodi.

Picropodophyllin has generally been considered to be biologically inactive, Ayres, D. C., and Loike, J. D., Lignana. Chemical, biological and clinical properties. Cambridge University Press, Cambridge, 1990.

OBJECTS OF THE INVENTION

The object of the invention is to find new methods for treatment of IGF-1R dependent diseases, especially cancer, by means of an inhibition of the tyrosine kinase of the insulin-like growth factor-1 receptor.

BRIEF DESCRIPTION OF THE DRAWINGS

FIG. 5A shows the effect on a melanoma cell line, FM 55, and a sarcoma cell line, RD-ES, respectively, and FIG. 5B the effect on two manipulated cell lines, R- and P6.

DESCRIPTION OF THE INVENTION

Figure 1:
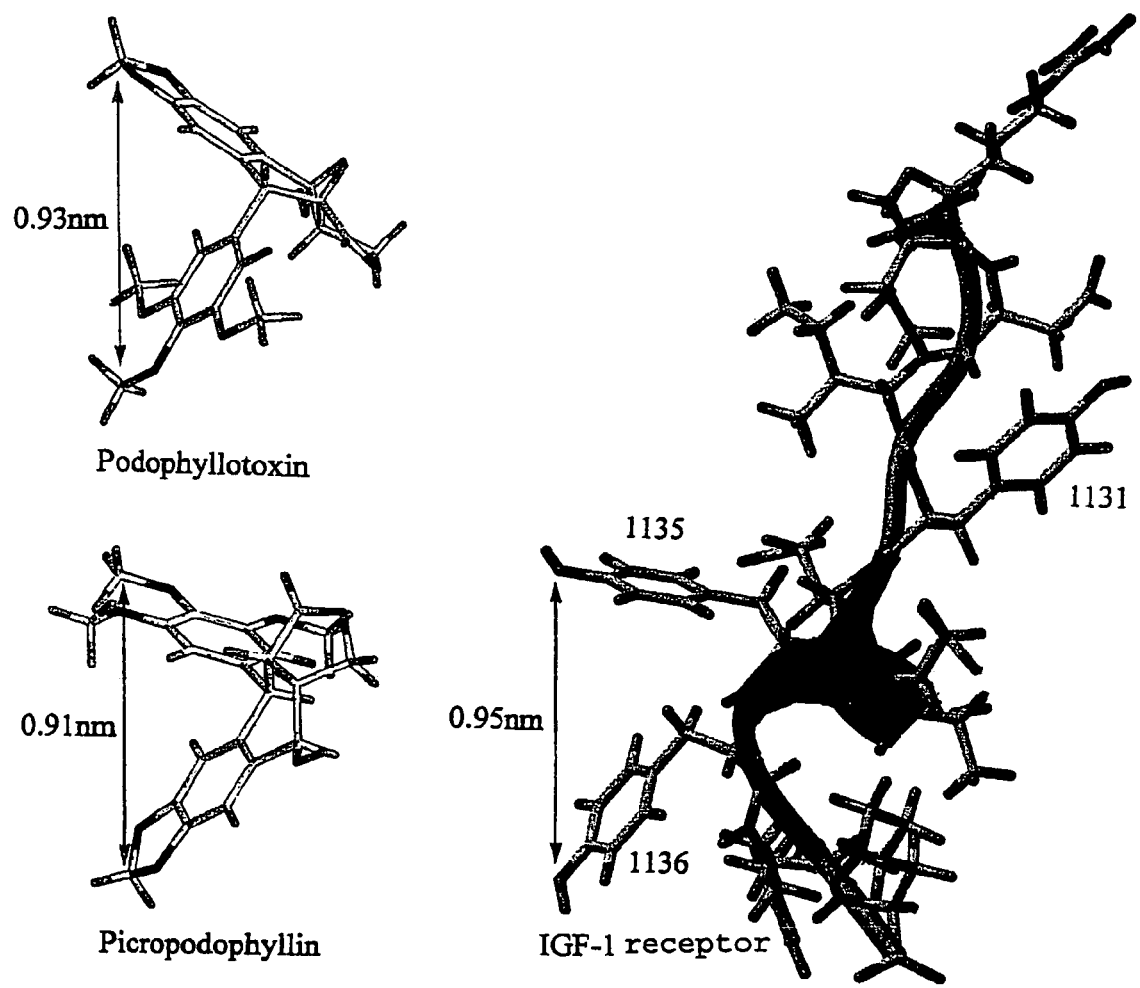
FIG. 1 shows a computer model of a 12 amino acid peptide comprising the tyrosines 1131, 1135 an 1136 of the IGF-1 receptor.
Figure 2A:
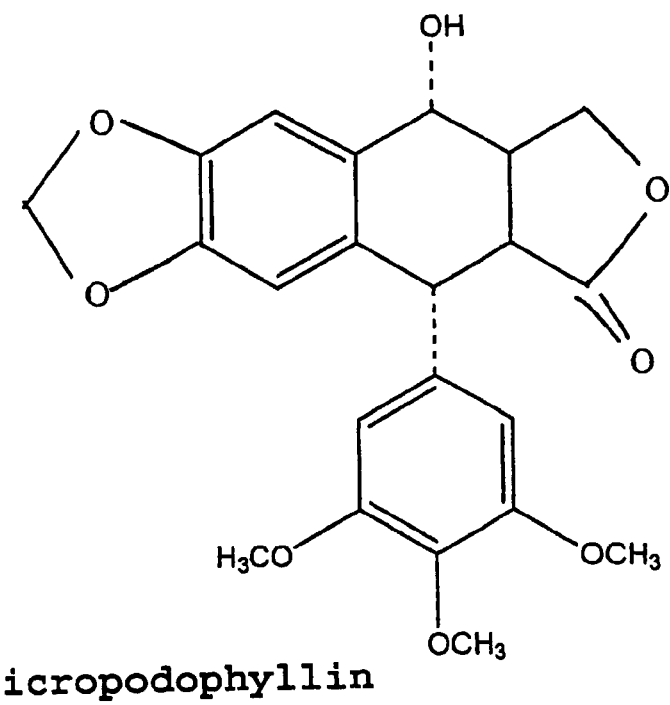
FIG. 2A shows the structural formulas of the compounds picropodophyllin and podophyllotoxin, and FIG. 2B the structural formulas of deoxypicropodophyllin and β-apopicropodophyllin.
Figure 2A:
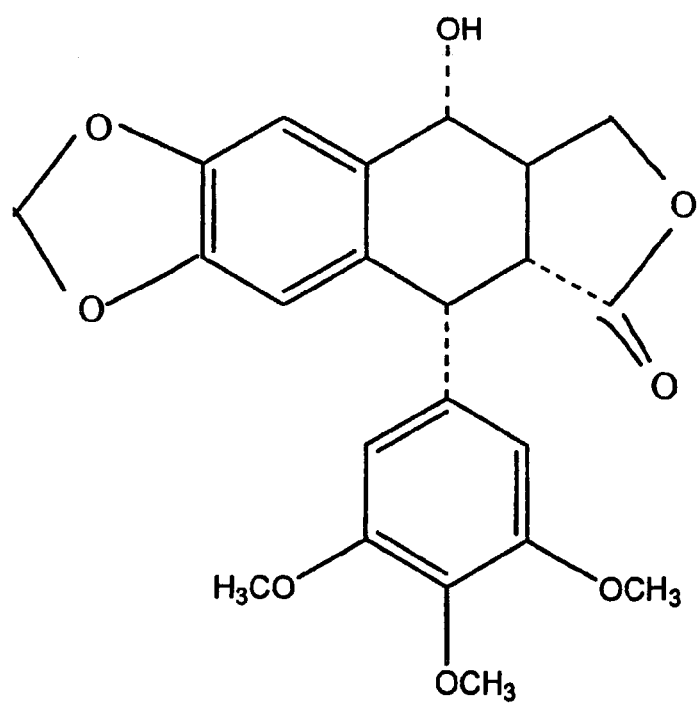
Figure 2B:
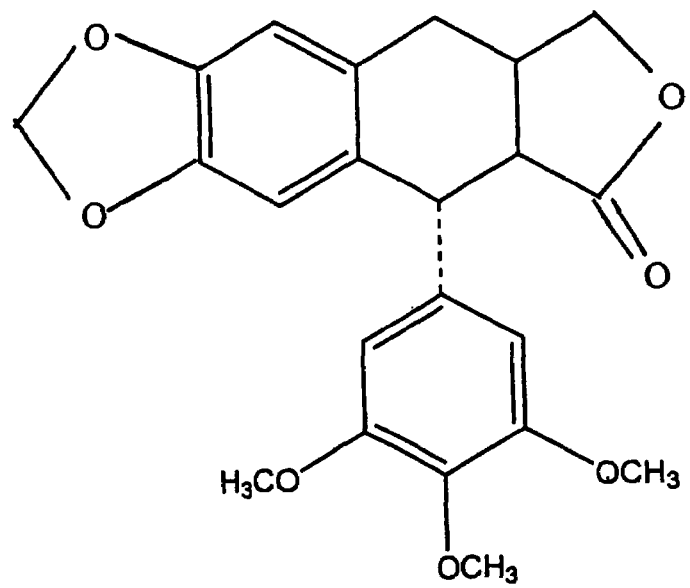
Figure 2B:
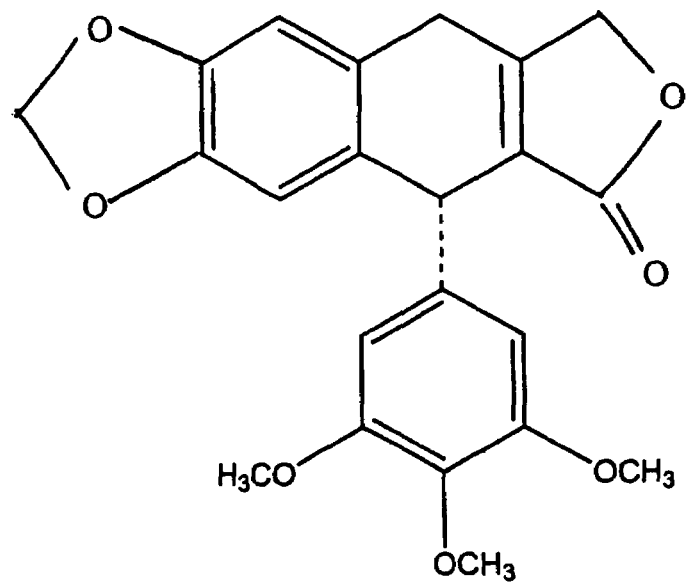

The three-dimensional structure of a 12-amino acid sequence of the IGF-1R tyrosine domain, including the tyrosine residues at position 1131, 1135 an 1136, was analysed using a computer programme in order to find compounds having the ability to mimick the tyrosine residues and interfere with the phosphorylation thereof. It was then discovered, when using a 12-amino acid peptide, that two of the three key tyrosines, that is 1135 and 1136, which have to be autophosphorylated in IGF-1R for activation, could be situated as close as 0.95 nm (9.5 Å) from each other, and that the apparent angle between these groups was about 60°. The configuration of said sequence is shown in FIG. 1. Such a short distance has not been observed for the corresponding tyrosines in the insulin receptor. FIG. 1 also depicts the space structure of podophyllotoxin and picropodophyllin.

Molecular modelling showed that an inhibitory molecule could consist of two benzene rings separated by only one carbon atom. When a two-carbon bridge was tried, the distance between the substituents of the benzene rings was too long, about 1.3 nm (13 Å).

The substituents corresponding to the hydroxy groups in the tyrosines were selected to be methoxy or methylenedioxy groups, since they are chemically relatively stable, i.e. they are not oxidized or phosphorylated. The distance between these substituents should be about 0.95±0.10 nm (9.5±1.0 Å).

It was then surprisingly found that two angled and substituted benzene rings of the cyclolignans podophyllotoxin and picropodophyllin fitted almost exactly into the pocket between tyrosine 1135 and 1136, indicating that said compounds could interfere with the autophosphorylation of the tyrosine residues. In contrast to the effect on microtubuli, the IGF-1R inhibition was not limited to cyclolignans with a trans configuration in the lactone ring.

In order to penetrate the receptor, an inhibitory molecule has to be small. When for instance podophyllotoxin was conjugated with a glucoside derivative, podophyllotoxin-4,6-O-benzylidene-β-D-glucopyranoside, the effect on IGF-1R completely disappeared. Furthermore, following reduction of the lactone ring to a diol structure, the size of the molecule increased due to the reduced substituents sticking out from the molecule, resulting in a dramatically reduced activity of the compounds. Increasing the size by forming methylenedioxy derivatives or acetonides of podophyllotoxin-diol also resulted in compounds with little or no activity.

The inhibitor molecule also has to be relatively non-polar, so that it can freely penetrate cell membranes and the IGF-1 receptor, but sufficiently polar to be reasonably soluble in water. The polarity of the molecule is determined by the number and nature of the oxygen functions. The polarity seems to be optimal when the water solubility is between that of deoxypodophyllotoxin, i.e. about 0.01 mM, and that of podophyllotoxin, about 0.1-0.2 mM. No charged or highly polar groups should be present on the molecule.

The invention refers to a compound of the formula I

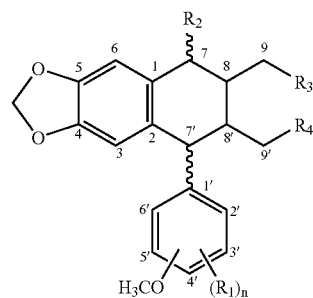

wherein $R_1$, which can be the same or different, is OH or $OCH_3$, n is 0, 1 or 2, $R_2$, $R_3$ and $R_4$, which can be the same or different, are H, OH, O, $OOCH_3$, $OOCH_2CH_3$, $OCH_3$, or $OC_2H_3$, or $R_3$ and $R_4$ together are an ether or a lactone, and which optionally contains a double bond $\Delta^{7(8)}$ or $\Delta^{8(8')}$, for use as a medicament.

Notably, the carbons in positions 9 and 9' of all the compounds of the formula I have a cis configuration, i.e. the 8-9 and 8'-9' bonds are located in or above the plane of the carbon ring (beta bonds), as indicated by the solid lines in the formula I. A wavy line, as between the carbons 1' and 7', indicates that the bond can be either an alpha or a beta bond. An alpha bond, that is below the plane of the carbon ring, is illustrated by a dashed line. The benzene ring should preferably be in α-position, as is demonstrated by picropodophyllin, deoxypicropodophyllin, α- and β-apopicropodophyllin.

The invention especially refers to compounds of the formula II,

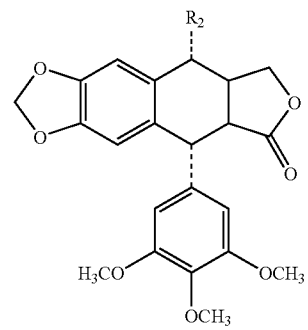

wherein $R_2$ is defined as in formula I, for use as a medicament. Preferred compounds are picropodophyllin or deoxypicropodophyllin. The chemical structure of said compounds is shown in FIG. 2.

Podophyllotoxin and deoxypodophyllotoxin, used as starting material for the synthesis of the described picro derivatives, are naturally occurring in plants. For the preparation of said substances in pure form, dried and finely ground rhizomes of e.g. Podophyllum emodi or Podophyllum peltatum are extracted with organic solvents. The extract is then filtered and concentrated on silica gel. The fractions containing the substances are collected and the latter are further purified by chromatography on acid alumina and silica gel etc., and finally recrystallized.

Deoxypicropodophyllin and picropodophyllin can be prepared from deoxypodophyllotoxin and podophyllotoxin, respectively. One mg of the latter was dissolved in 70% aqueous methanol. To the solution was added 20 mg of sodium acetate and the mixture was then incubated for 20 h at 55° C. After evaporation of the alcohol, the product was extracted with ethyl acetate, and then purified by chromatography on silica gel, mobile phase: hexane-ethyl acetate mixtures, and/or octadecylsilane-bonded silica, mobile phase: aqueous methanol; HPLC).

Other compounds of the invention of special interest for use as a medicament can be described by the following formula III

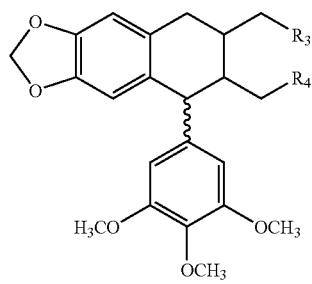

III wherein $R_3$ and $R_4$ are defined as in formula I, and which in addition contains a double bond $\Delta^{7(8)}$ or $\Delta^{8(8')}$, for use as a medicament. Preferred compounds of the formula III are α-apopicropodophyllin and β-apopicropodophyllin.

α- and β-apopicropodophyllin can be prepared from podophyllotoxin by incubation in a buffered ethanolic solution at elevated temperature, as described by Buchardt, O. et al., *J Pharmaceut Sci* 75, 1076-1080, 1986. The total synthesis of picropodophyllin and its apo derivatives have been described by Gensler, J. W., et al., *J Am Chem Soc* 82, 1714-1727, 1960.

As additional examples of compounds of the formula I can be mentioned: epipicropodophyllin, picropodophyllone, 4'-demethylpicropodophyllin, and the acetate derivative of picropodophyllin and the methyl ester and ethyl ester derivatives of picropodophyllic acid.

The invention especially refers to the use of a compound of the formula I for the preparation of a medicament inhibiting tyrosine phosphorylation of the insuline-like growth factor-1 receptor.

Figure 3:
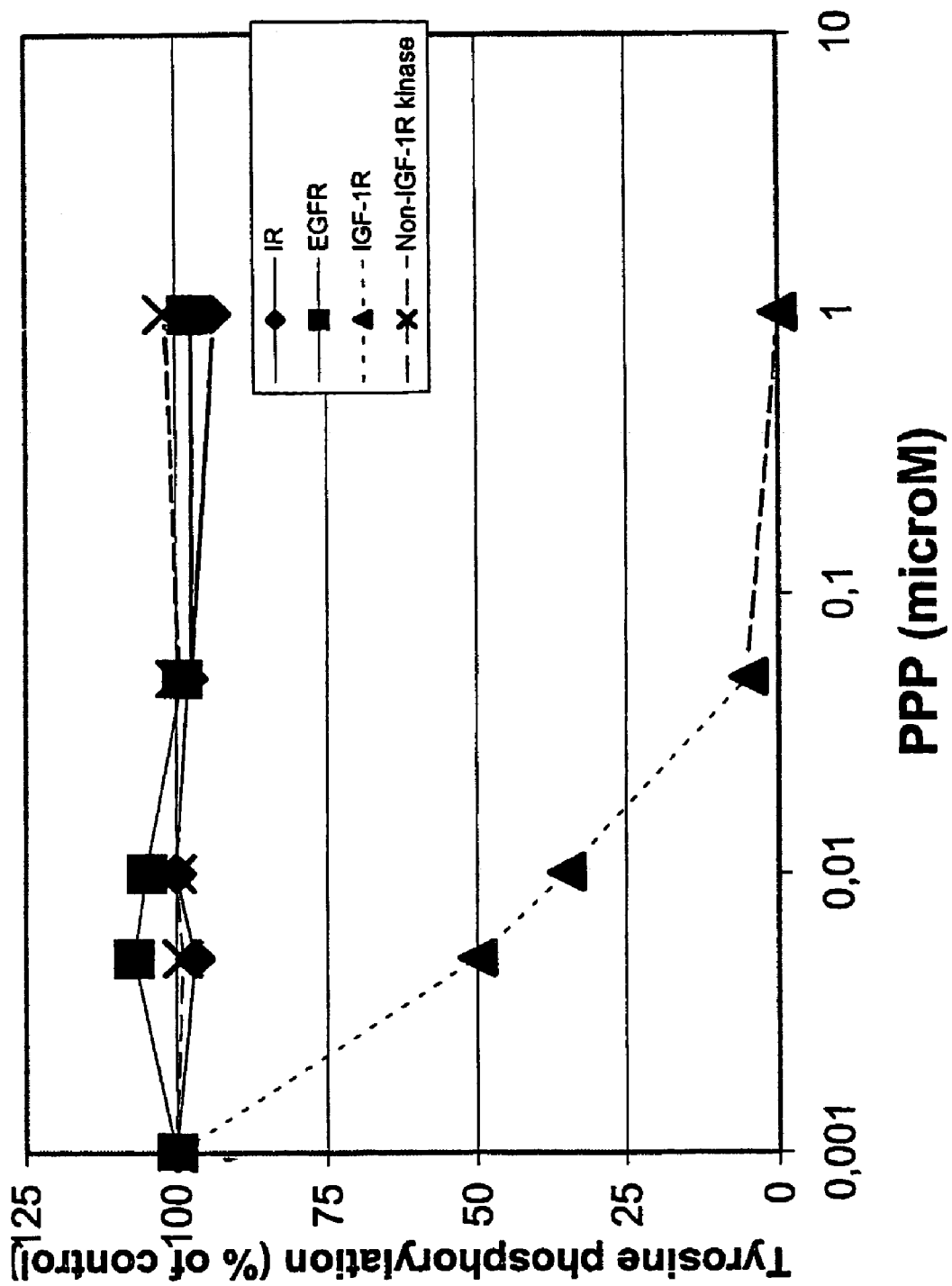
FIG. 3 is a diagram showing the effect of picropodophyllin on tyrosine phosphorylation of different receptors.

TO design an inhibitor of the IGF-1R tyrosine kinase for therapeutic purposes it is of critical importance that the inhibitor does not cross-react with the insulin receptor kinase, which is highly homologous to the IGF-1R. Co-inhibition of the insulin receptor will lead to a diabetogenic response in vivo. This response comprises a very serious side effect, which cannot be overcome by insulin treatment since the receptor kinase is being blocked. It has, however, now been demonstrated, see FIG. 3, that picropodophyllin, which is a much more potent IGF-1R inhibitor than the tyrophostin-based compounds, does not at all interfere with the insulin receptor tyrosine kinase. Nor does it interfere with tyrosine phosphorylation of the epidermal growth factor, platelet-derived growth factor or fibroblast growth factor receptors.

According to a preferred aspect the invention refers to the use of a compound as described above for the preparation of a medicament for prophylaxis or treatment of IGF-1R dependent diseases, such as cancer, artheriosclerosis, including prevention of restenosis of the coronary arteries after vascular surgery, psoriasis and acromegaly.

Podophyllotoxin has for long been implicated in cancer therapy, but produced unacceptable side effects. The anticancer effect, as well as the side effects, was attributed to inhibition of microtubule assembly and mitotic block. It has now been demonstrated that podophyllotoxin and its non-toxic isomer picropodophyllin, which has generally been considered to be biologically inactive, are very potent and specific inhibitors of tyrosine phosphorylation of the insulin-like growth factor-1 receptor, which plays a pivotal role as a survival factor in cancer cells. Of utmost importance is that neither picropodophyllin nor other picro derivatives having a cis configuration in the lactone ring inhibit the insulin receptor, which is highly homologous to IGF-1R. Nor do they inhibit other major growth factor receptor kinases. The low general cytotoxicity of picropodophyllin compared with podophyllotoxin suggests that the former compound is a very selective IGF-1R inhibitor.

The results of the biological experiments suggest that submicromolar concentrations of picropodophyllin or other picro derivatives can be sufficient to cause tumor cell death. However, for optimal treatment it is believed that it is important to keep a relatively constant concentration of the inhibitors over lengthy periods, to allow them to continuously saturate all IGF-1Rs, and in this way eventually kill as many malignant cells as possible. Therefore, infusion of picropodophyllin or derivatives, in connection with monitoring the plasma concentration of the compound, may be the strategy of choice instead of repetetive (e.g. daily) administrations, which may lead to reactivations of IGF-1R between the treatments.

Previous attempts to treat humans and animals with podophyllotoxin have demonstrated that this is a relatively toxic compound, both systemically ($LD_{50}$ for rats is 14 mg/kg) and locally (tissue-damaging). Its cytotoxicity has been linked to its binding to β-tubulin, but this should only occur at much higher concentrations than those required for IGF-1R-inhibition when tested in vitro ($IC_{50}$ of 0.5-1.0 μM versus $IC_{50}$ of 0.001 μM). This toxicity precludes its use as a drug for parenteral, per oral, and topical administration.

The invention especially refers to the use of a compound as described for the preparation of a medicament for prophylaxis or treatment of different types of cancer, such as malignant melanoma; primitive neuroectodermal tumors, such as Ewing's sarcoma; gliomas, such as glioblastoma and astrocytoma; prostate carcinoma; breast carcinoma; myeloproliferative and lymphoproliferative diseases, such as leukemias and lymphomas; gastrointestinal tumors, such as gastric cancer, colonic cancer and pancreatic carcinoma; gynecological cancer, such as ovarial cancer and endometric carcinoma.

In case of tumors not completely dependent on IGF-1R, the compounds of the invention can be useful to potentiate the effects of other anti-cancer drugs. The invention therefore also refers to the use of a compound of the formula I in combination with another cytostaticum. As examples of cytostatica which can be used together with a cyclolignan of the invention can be mentioned vincristin, taxol and etoposide.

According to a special aspect the invention refers to the use of compounds of the formula III for the preparation of a medicament for treatment of leukemia.

In addition to cancer therapy, the cyclolignans may be valuable for treatment of other diseases, the pathogenesis of which involves IGF-1/IGF-1R, like artheriosclerosis and psoriasis, see for instance Bayes-Genis, A., et al., *Circ Res* 86, 125-30 (2000).

According to a special aspect the invention refers to the use of compounds of the formula I for the preparation of a medicament for treatment of psoriasis. Epidermal hyperplasia is a key feature of the common skin disorder psoriasis. Stimulation of epidermal keratinocytes by IGF-1 is essential for cell division and increased sensitivity to IGF-1 may therefore occur in psoriasis. In a recent study IGF-1R antisense oligonucleotides were injected into human psoriasis lesions, and this treatment caused a dramatic normalization of the hyperplastic epidermis, Wraight, C. J., et al.; *Nat Biotechnol* 18, 521-6 (2000). This strongly suggest that IGF-1R stimulation is a rate-limiting step in psoriatic epidermal hyperplasia and that IGF-1R targeting by selective inhibitors can form the basis of a potential new psoriasis therapy.

According to another aspect the invention refers to the use of compounds of the formula I for the preparation of a medicament for treatment of artheriosclerosis and restenosis following coronary angioplasty. IGF-1 is a growth promoter for arterial cells and a mediator of cardiovascular disease, such as artheriosclerotic plaque development and restenosis after coronary angioplasty. IGF-1 promotes macrophage chemotaxis, excess LDL cholesterol uptake, and release of proinflarmatory cytokines. Furthermore, IGF-1 stimulates vascular smooth muscle cell (VSMC) proliferation and migration to form a neointima. Thus, IGF-1 seems to play a key role in these events and in order to limit or reverse plaque growth and vulnerability in artheriosclerosis and in the neointimal hyperplasia of restenosis, the activity of IGF-1 can be suppressed by using the IGF-1R inhibitors. (Bayes-Genis, A., et al., *Circ Res* 86, 125-130, 2000.)

The invention also refers to a pharmaceutical composition comprising a compound of the formula I in combination with a physiologically acceptable carrier. The pharmaceutical composition, which optionally contains conventional additives, can be administered to a patient by any suitable route, depending on the disease being treated and the condition of the patient.

For parenteral administration, the compounds may be administered as injectable dosages or by continous intravenous infusion of a solution, suspension or emulsion of the compound in a physiologically acceptable diluent as the pharmaceutical carrier, which can be a sterile liquid, such as water, alcohols, oils, and other acceptable organic solvents, with or without the addition of a surfactant and other pharmaceutically acceptable adjuvants.

The compounds can also be administered in the form of a depot injection or implant preparation, which may be formulated in such a manner as to permit a sustained release of the active ingredient.

For oral administration, the compounds can be formulated into solid or liquid preparations such as capsules, pills, tablets, troches, powders, solutions, suspensions or emulsions.

For topical application the compounds can be administered in the form of an unguent, cream, ointment, lotion or a patch.

The invention consequently also refers to a method of treatment of a cancer in a mammal, comprising the steps of administrating a pharmaceutical composition, containing a compound having the formula I in combination with a physiologically acceptable carrier, by constant infusion to a patient suffering from a tumor, controlling the plasma level of the compound, and adjusting the rate of infusion to keep the plasma level at a concentration of 0.05-5.0 µM, for a period of time being sufficient for the tumor to be retarded or to disappear.

EXPERIMENTAL

Materials
 Chemicals
  Cell culture reagents, that is media, fetal calf serum and antibiotics, were purchased from Gibco, Sweden. All other chemicals unless stated otherwise were from Sigma (St. Louis. Mo., USA). A mouse monoclonal antibody against phosphotyrosine (PY99) and a polyclonal antibody against α-subunit of IGF-1R (N20) and α-subunit of the insulin receptor, and a polyclonal antibody against the platelet-derived growth factor receptor were obtained from Santa Cruz Biotechnology Inc (Santa Cruz, Calif., USA). A monoclonal antibody against the α-subunit of IGF-1R (αIR-3) and a monoclonal antibody to fibroblast growth factor receptor were purchased from Oncogene Science (Manhasset, N.Y., USA). The murine monoclonal antibody against the epidermal growth factor receptor was purchased from Life Science and the Anti-IRS-1 agarose conjugate antibody was obtained from UBI (Lake Placid, N.Y., USA).

($^3$H)Thymidine and ($^3$H)leucine were from Amersham Int.(UK) and the monoclonal antibody against α-smooth muscle actin was from Sigma Immuno Chemicals (La Jolla, Calif., USA). Recombinant IGF-1 was a gift from Pharmacia Upjohn (Stockholm, Sweden). Deoxypodophyllotoxin and podophyllotoxin (99.97% purity), and α-apopicropodo-Pre Jorat, Switzerland and so was podophyllotoxin-4,6-O-benzylidene-p-D-glucopyranoside from Conpharm AB, Uppsala, Sweden. Etoposide, was from Sigma.

Cell cultures
  The human melanoma cell lines SK-MEL-2, SK-MEL-5 and SK-MEL-28, the Ewing's sarcoma cell lines RD-ES and ES-1, the hepatoma cell line HepG2, the prostatic carcinoma cell line PC-3, and the breast cancer cell line MCF-7 were from the American Tissue Culture Collection, USA. The malignant melanoma cell lines BE, DWB and FM 55 were obtained from Professor R Kiessling, CCK, Karolinska Hospital, Stockholm, Sweden. The R- and P6 cell lines were gifts from Professor R. Baserga, Thomas Jefferson University, Philadelphia, Pa., USA. R-cells are IGF-1R negative, whereas P6 cells overexpress the IGF-1R.

Keratinocytes (HaCaT cells) were provided by and tested in collaboration with Professor Mona Bäckdahl, Department of Dermatology, Karolinska Hospital, Stockholm, Sweden. The HaCaT cell line is a spontaneously immortalized human keratinocyte cell line (Boukamp P, et al., *J Cell Biol* 106: 761-771, 1988), which is frequently used as an experimental model for psoriasis (Wraight, C. J., et al. *Nat Biotechnol* 18: 521-526, 2000.) HaCaT cells were cultured in Dulbecco's Modified Eagle's Medium containing 10% fetal bovine serum, glutamine, benzylpenicillin and streptomycin.

Human vascular smooth muscle cells (VSMC) were isolated and cultured from surgical specimen of human renal artery essentially as described previously (Ross R., *J Cell Biol* 50: 172-186, 1971). Briefly, VSMC were allowed to migrate from the primary explants and were subsequently passaged at confluence. Cells were maintained in F12 medium containing 15% fetal bovine serum, 0.05 mg/ml ascorbic acid, 2 µg/ml fungizone and 200 IU/ml of penicillin. Cultured cells were a uniform population of human smooth muscle cells identified both by their morphology and by immunostaining for smooth muscle specific alfa-actin, which recognizes a unique epitope. Culturing was performed at a temperature of 37° C., humidity of 85% and at a $CO_2$ concentration of 5% in air. The medium was changed twice a week and the cells were harvested at passage 2 to 8 using a solution of trypsin (0.25%) and EDTA (0.02%).

The human chronic myeoloid leukemia K562/S and K562/Vcr30 lines and the acute myeloid leukemia cell lines HL60/0 and HL60/Nov were obtained from ATCC. The K562/S and K562/Vcr30 are wild type (non-resistent) cells, whereas K562/Vcr30 and HL60/Nov are cytostatic-resistant sublines. All leukemia cell lines were cultured in RPMI 1640 medium supplemented with 10% fetal bovine serum and with 2 mM L-glutamine, benzylpenicillin (100 U/ml) and streptomycin (100 µg/ml). The cells were grown in tissue culture flasks maintained at 95% air/5% $CO_2$ atmosphere at 37° C. in a humidified incubator. For the experiments cells were cultured in 60-mm plastic dishes or 96-well plastic plates.

All other cell lines were cultured in Minimal Essential Medium containing 10% fetal bovine serum, glutamine, 1% benzylpenicillin and streptomycin. The cells were grown in monolayers in tissue culture flasks maintained at 95% air/ 5% $CO_2$ atmosphere at 37° C. in a humidified incubator. For the experiments cells were cultured in either 35-mm or 60-mm plastic dishes or 96-well plastic plates. The experiments were initiated under subconfluent growth conditions.

Methods

In vitro tyrosine kinase assays

IGF-1R-catalyzed substrate phosphorylation of polyTyr-Glu (pTG) was performed essentially as previously described [Parrizas M., et al., ibid., and Blum G., et al., ibid.]. Immunoprecipitated IR from HepG2, IGF-1R from P6 cell extract and immunodepleted supernatant to assay non-IGF-1R tyrosine kinases. The phosphorylated polymer substrate was probed with a purified phosphotyrosine specific monoclonal antibody conjugated to horseradish peroxidase (HARP). Color was developed with HRP chromogenic substrate o-phenylenediamine dihydrochloride (OPD). The color was quantitated by spectrophotometry (ELISA reader) and reflects the relative amount of tyrosine kinase. The precipitate was immunoblotted with antibodies to IGF-1R and IR to verify the presence of the receptor. Serial dilutions were used to assay the optimal conditions with respect to the amount of IGF-1R and IR. The signal was linear for 30 minutes and was a function of IGF-1R concentration up to 75 ng/well. Briefly, 96 well plates (Immunolon, Nunc) were coated overnight at 4° C. with a mouse monoclonal antibody (LabVision) against the beta-subunit of IGF-1R at a concentration of 1 µg/ml. The plates were blocked with BSA in PBS (ELISA blocking buffer, Pierce), and 80 µg/ml of total protein lysate from the P6 cell line was added. The plates were incubated for 1 h, and washed with PBS Tween. The investigated compounds were added in PBS at room temperature for 30 minutes, prior to kinase activation with IGF-1. Kinase assay was performed using the Sigma kit for in vitro phosphorylation following the manufacturer instructions. After spectrophotometry the $IC_{50}$ values of inhibitors were determined using the Regression function of Statistica program.

IGF-1R tyrosine autophosphorylation was analysed by a sandwich ELISA assay. Briefly, 96-well plates (Immunolon, Nunc) were coated overnight at 4° C. with 1 µg/well of the monoclonal antibody Ab-5 (LabVision) to the IGF-1R beta subunit. The plates were blocked with 1% BSA in PBS Tween for 1 h, then 80 g/well of total protein lysate from the P6 cell line was added. As a negative control was used total protein lysate from the R-cell line. The investigated compounds were added in tyrosine kinase buffer without ATP at room temperature for 30 min, prior to kinase activation with ATP. Kinase assay was performed using the Sigma kit. After spectrophotometry the IC50 values of inhibitors were determined using the Regression function of Statistica program.

Assay of cell growth and survival

Cell proliferation kit II (Roche Inc.) is based on colorimetric change of the yellow tetrazolium salt XTT in orange formazan dye by the respiratory chain of viable cells (Roehm, NW, et al., *J Immunol Methods* 142:257-265, 1991). Cells seeded at a concentration of 5000/well in 100 µl medium in a 96-well plate were treated with different drugs in the given concentration. After 24 or 48 h the cells were incubated, according to the manufacturer's protocol, with XTT labelling mixture. After 4 h the formazan dye is quantified using a scanning multiwell spectrophotometer with a 495 nm filter. The absorbance is directly correlated with the number of viable cells. The standard absorbance curve was drawn by means of untreated cells seeded at a concentration of from 1000%o 10 000 cells/well with an increasing rate of 1000 cells/well. All standards and experiments were performed in triplicates.

Assay of tyrosine phosphorylation of receptors in intact cells

Cells were cultured to subconfluency in 6-cm plates, and then fresh medium containing 10% FBS and the desired compounds were added for 1 h. The cells were then lyzed and subjected to immunoprecipitation using specific antibodies. Immunoprecipitates were resolved by sodium dodecyl sulphate polyacrylamide gel electrophoresis (SDS-PAGE) and transferred to nitro-cellulose membranes and incubated with anti-phosphotyrosine antibody. Antibodies to actin (in cell extract) or IGF-1R beta subunit were used as loading controls. After detection the films were scanned for quantification.

Immunoprecipitation and determination of protein content

The isolated cells were then lyzed in 10 ml ice-cold PBSTDS containing protease inhibitors (Carlberg, M., et al., *J Biol Chem* 271:17453-17462, 1996). 50 µl protein A or G agarose was added in 1 ml sample and incubated for 15 min at 4° C. on an orbital shaker. After centrifugation for 10 min at 10,000 r/min at 4° C. the supernatant was saved. The protein content was determined by a dye-binding assay with a reagent purchased from Bio-Rad. Bovine serum albumin was used as a standard. 15 µl Protein G Plus agarose and 5 µl anti-IGF-1R were added. After a 3 h incubation at 4° C. on an orbital shaker the precipitate was collected by pulse centrifugation in a micro centrifuge at 14,000× g for 10 s. The supernatant was discarded and the pellet was washed 3 times with PBSTDS.

Sodium dodecyl sulphate polyacrylamide gel electrophoresis (SDS-PAGE)

Protein samples were solved in a 2×-sample buffer containing Laemmli buffer and 0.5% methanol and boiled for 5 min at 96° C. Samples were separated by SDS-PAGE with a 4% stacking gel and 7.5% separation gel. Molecular weight markers (Bio Rad, Sweden) were run simultaneously in all experiments.

Western blotting

Following SDS-PAGE the proteins were transferred overnight to nitro-cellulose membranes (Hybond, Amersham, UK) and then blocked for 1 h at room temperature in a solution of 4% skimmed milk powder and 0.02% Tween 20 in PBS, pH 7.5. Incubations with the primary antibodies were performed for 1 h at room temperature, followed by 3 washes with PBS with Tween and incubation with the second antibody for 1 h room temperature. After another 3 washes the membranes were incubated with Streptavidin-labelled horseradish peroxidase for 30 min and then detected using Amersham ECL system (Amersham, UK). The films were scanned by Fluor-S (BioRad).

Experiment 1. Effect of podophyllotoxin derivatives on phosphorylation of IGF-1R in cultured melanoma cells FM55 melanoma cells were seeded in 6-cm dishes, at a concentration of 10,000 cells/cm$^2$ in Minimal Essential Medium supplemented with 10% fetal calf serum (FCS). When the cells reached a density of 65,000 cells/cm$^2$ in the dishes, they were treated for 1 h with 0.05 μM podophyllotoxin, deoxypodophyllotoxin, picropodophyllin, deoxypicropodophyllin, 4'-demethyl-7-(4,6-O-ethylidene-β-D-glucopyranosyl)epipodophyllotoxin (etoposide) and Etoposide and pf-4,6-O were also administered at 15 μM. The cells were then harvested for assay and quantification of IGF-1R phosphorylation as described under Methods. The values shown in Table 1 represent means of 3 experiments.

TABLE 1

Level of IGF-1R phosphorylation in intact cells (% OD)

| | |
|---|---|
| Podophyllotoxin | 5 |
| Deoxypodophyllotoxin | 2 |
| Picropodophyllin | 8 |
| Deoxypicropodophyllin | 5 |
| Etoposide (0.05 μM) | 102 |
| Etoposide (15 μM) | 105 |
| Pf-4,6-O (0.05 μM) | 100 |
| Pf-4,6-O (15 μM) | 102 |

The results show that podophyllotoxin, deoxypodophyllotoxin, picropodophyllin and deoxypicropodophyllin are all potent inhibitors of IGF-1R phosphorylation, while etoposide and Pf-4,6-O are not.

Experiment 2. Dose-response effect of picropodophyllin on phosphorylation of IGF-1R in a cell-free system All these data on intact cells showed that picropodophyllin and podophyllotoxin prevented phosphorylation of IGF-1R, but did not reveal if this was a direct or an indirect effect on the tyrosine kinase. Therefore we isolated the receptor and determined the effects of picropodophyllin on IGF-1R catalyzed substrate tyrosine phosphorylation and IGF-1R autophosphorylation in-vitro. Picropodophyllin efficiently decreased the phosphorylation of the pTG substrate (IC$_{50}$ value 0.006 μM, see FIG. 3). In contrast, it failed to interfere with substrate phosphorylation of EGFR and IR tyrosine kinases, as well as that of other 'non-IGF-1R kinases' (FIG. 3), which were obtained by immunodepletion of IGF-1R. Podophyllotoxin produced similar results as picropodophyllin.

Figure 4:
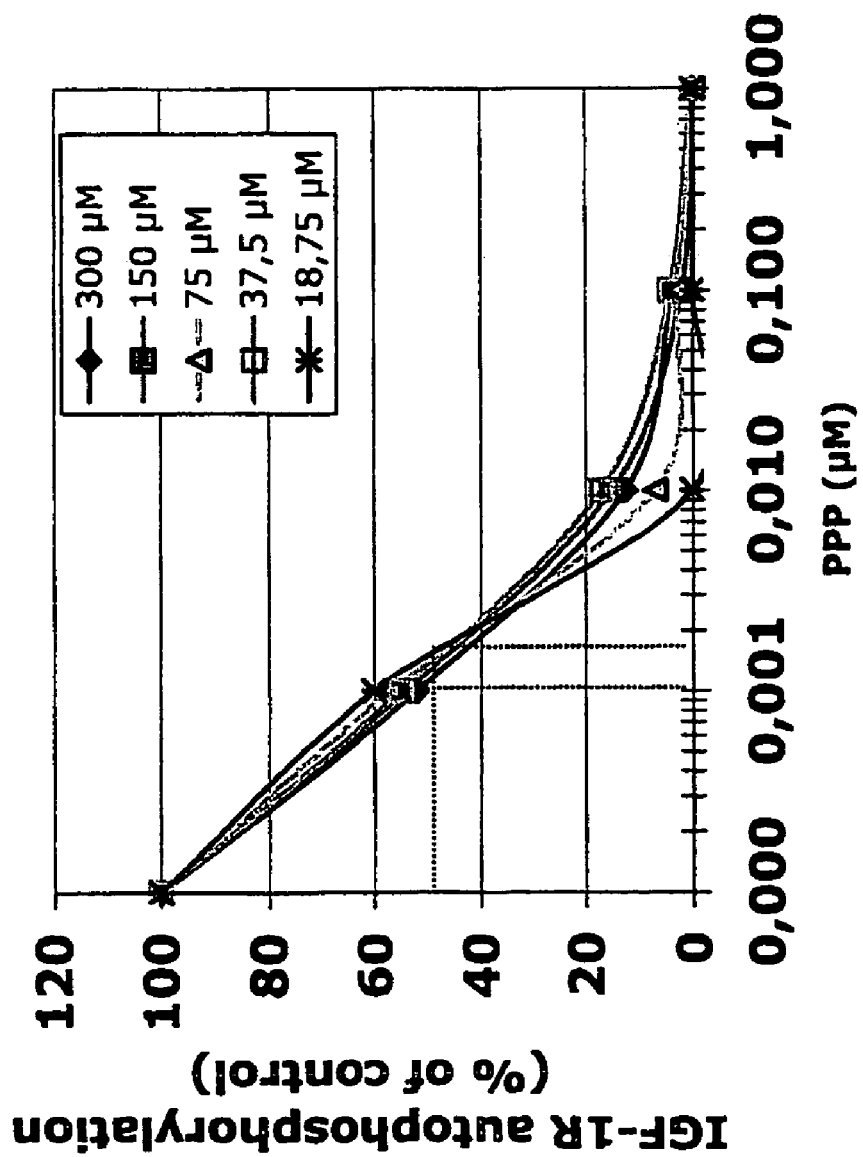
FIG. 4 is a diagram showing the effect of picropodophyllin on the autophosphorylation of IGF-1R.

In the next set of cell-free experiments we demonstrated that PPP efficiently inhibited the autophosphorylation of IGF-1R (for details see Methods), with an IC$_{50}$ value of around 0.001 μM (see FIG. 4). A similar response was obtained by PPT (data not shown). To investigate whether PPP interferes with the tyrosine autophosphorylation at the ATP level or at the substrate level (i.e., the tyrosine kinase domain of the IGF-1R β-subunit), various concentrations of ATP (19-300 μM) were added to the reaction buffer during the assay. As shown, this did not alter the IC$_{50}$ value of PPP, which remained at 0.001-0.002 μM (FIG. 4). These results imply that the inhibitors of IGF-1R autophosphorylation do not act by interfering with ATP, but rather inhibit substrate phosphorylation by the IGF-1R tyrosine kinase.

Experiment 3. Specificity of picropodophyllin and podophyllotoxin on various receptor tyrosine kinases in cultured cells FM55 melanoma cells were cultured in the same way as described in Experiment 1. When reaching a density of 65,000 cells/cm$^2$ in the dishes, they were treated for 1 h with 0 (control) and 0.05 μM of picropodophyllin and podophyllotoxin, respectively. The cells were then isolated and subjected to immunoprecipitation of the IGF-1R, fibroblast growth factor receptor (FGFR), platelet-derived growth factor receptor (PDGFR), epidermal growth factor receptor (EGFR), insulin receptor (IR) and insulin substrate-1 (IRS-1) using antibodies to respective molecules. IRS-1 is a substrate of IGF-1R, and therefore its phosporylation is dependent on phosphorylated IGF-1R. Gelelectrophoresis, Western blotting and quantification of the different signals were performed as described above.

TABLE 2

Level of IGF-1R phosporylation in intact cells (% OD)

| | Picropodophyllin (PPP) and Podophyllotoxin (PPT) 0.05 μM | |
|---|---|---|
| Substrate | PPT | PPP |
| IGF-1R | 7 | 20 |
| FGFR | 105 | 100 |
| PDGFR | 100 | 104 |
| EGFR | 107 | 106 |
| IR | 101 | 100 |
| IRS-1 | 10 | 17 |

This demonstrates that picropodophyllin and podophyllotoxin are specific for IGF-1R.

Experiment 4. Effects of podophyllotoxin and picropodophyllin on IGF-1R phosphorylation of various malignant cell types 12 cell lines of different origins were seeded in 6-cm dishes, at a concentration of 10,000 cells/cm$^2$ in Minimal Essential Medium supplemented with fetal calf serum (FCS). When the cells had reached a concentration of 65,000 cells/cm$^2$, they were treated with 0, 0.01, 0.025, 0.05, 0.1 or 1.0 μM doses of podophyllotoxin and picropodophyllin for 1 h. The cells were then harvested for assay and quantification of IGF-1R phosphorylation as described above. The EC50 value, the Efficient Concentration 50%, i.e. the , concentration needed to reduce the phosphorylation with 50%, for each inhibitor and cell line, is then calculated. The values are shown below in Table 3. The results are based on two different experiments.

TABLE 3

EC50 for IGF-1R phosphorylation

| Cell line | Origin | Podophyllotoxin | Picropodophyllin |
|---|---|---|---|
| SK-MEL-2 | melanoma | 0.04 | Nd |
| SK-MEL-5 | melanoma | 0.03 | 0.04 |
| SK-MEL-28 | melanoma | 0.03 | 0.04 |
| BE | melanoma | 0.04 | nd |
| FM55 | melanoma | 0.04 | 0.06 |
| DWB | melanoma | 0.03 | nd |
| MCF-7 | Breast cancer | 0.05 | 0.04 |
| PC-3 | prostate cancer | 0.06 | 0.09 |
| RD-ES | Ewing's sarcoma | 0.03 | 0.05 |
| HepG2 | hepatoblastoma | —* | —* |

TABLE 3-continued

EC50 for IGF-1R phosphorylation

| Cell line | Origin | Podophyllotoxin | Picropodophyllin |
|---|---|---|---|
| R- | IGF-1R negative fibroblasts | —* | —* |
| P6 | fibroblasts with overexpressed IGF-1R | 0.02 | 0.03 |

*No IGF-1R activity in controls. nd, not determined

This shows that podophyllotoxin and picropodophyllin inhibits IGF-1R phosphorylation in various cancer cells.

Figure 5A:
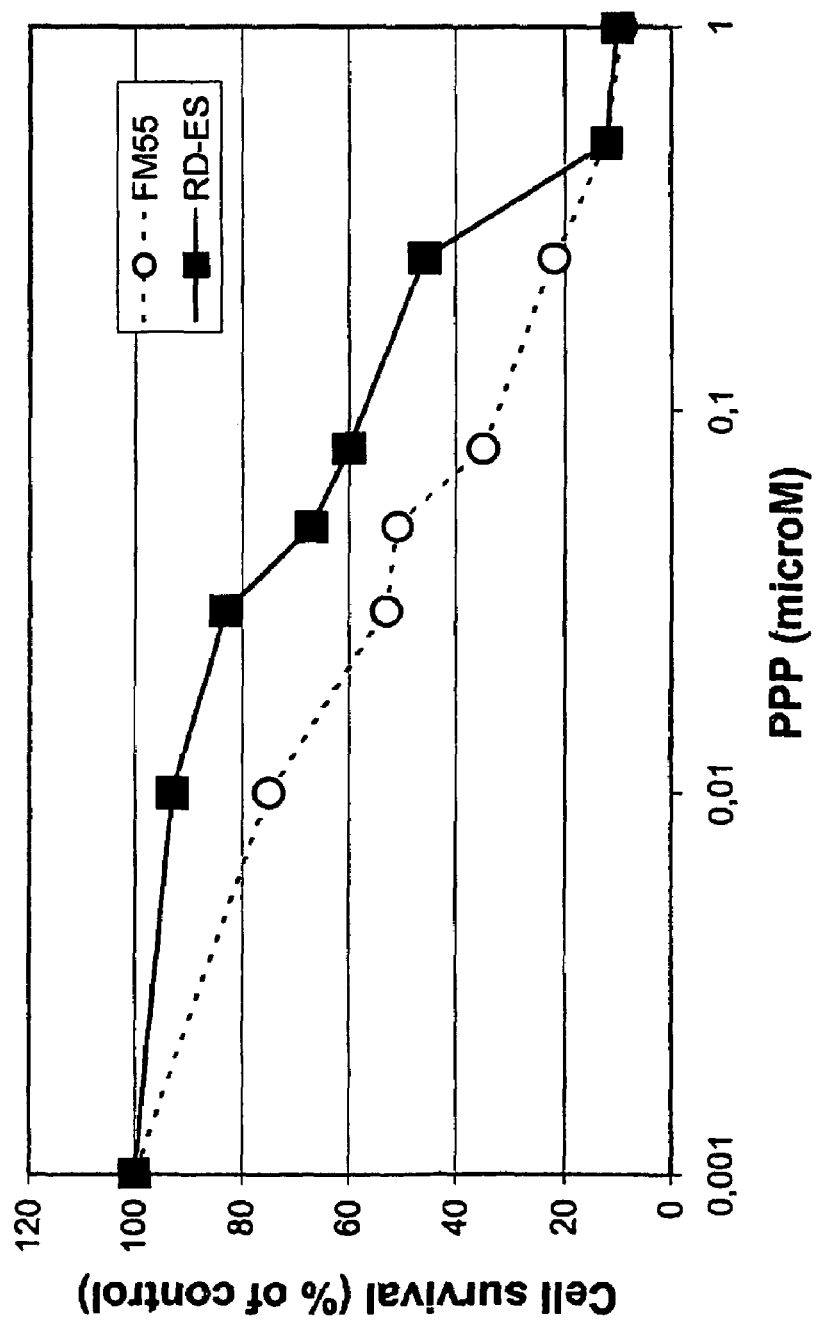
FIGS. 5A and 5B are diagrams showing the dose-response effects of picropodophyllin on the viability of 4 different cell lines.
Figure 5B:
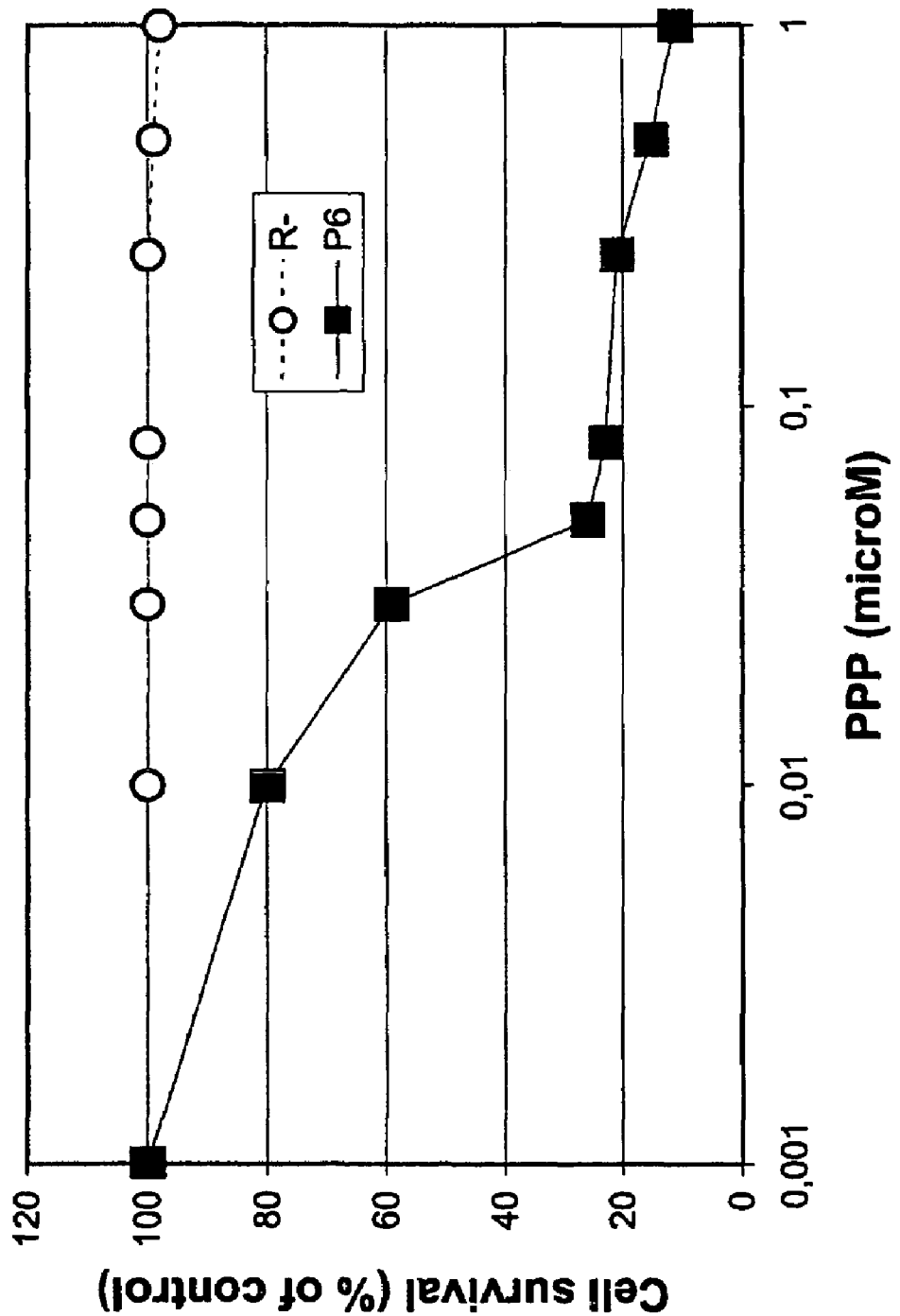

Experiment 5. Effects of podophyllotoxin and picropodophyllin on viability of a large number of malignant cell types 12 different types of cell lines were seeded in 96-well plates (medium volume in a well was 100 µl), at a concentration of 10,000 cells/cm$^2$ in Minimal Essential Medium supplemented with fetal calf serum. When the cells had reached a concentration of 65,000 cells/cm$^2$, they were treated with different doses of podophyllotoxin and picropodophyllin for 48 h. Cell viability was then assayed (see above). EC50 values for each inhibitor and cell line, calculated as the concentration, resulting in a 50% decrease in cell survival, are shown below in Table 4. The dose-response curves for the melanoma cell line FM55 and the Ewing's sarcoma cell line RD-ES treated with picropodophyllin are depicted in FIG. 5A. The viability of both tumor cell lines is decreased by the picropodophyllin concentration. FIG. 5B demonstrates the dose-response curves for a murine fibroblast cell line, either devoid of (R-) or overexpressing the human IGF-1R (P6). Whereas the viability of P6 cells drops with picropodophyllin dose, the R-cells are not responsive. This implies that picropodophyllin is selective for the IGF-1R. All results presented in Table 4 and FIG. 5 are based on 4 different experiments.

TABLE 4

EC50 (µM) for cell viability

| Cell line | Origin | Podophyllotoxin | Picropodophyllin |
|---|---|---|---|
| SK-MEL-2 | melanoma | 0.05 | Nd |
| SK-MEL-5 | melanoma | 0.02 | 0.05 |
| SK-MEL-28 | melanoma | 0.02 | 0.03 |
| BE | melanoma | 0.05 | nd |
| FM55 | melanoma | 0.04 | 0.07 |
| DWB | melanoma | 0.04 | nd |
| MCF-7 | breast cancer | 0.07 | 0.09 |
| PC-3 | prostate cancer | 0.06 | 0.09 |
| RD-ES | Ewing's sarcoma | 0.10 | 0.10 |
| HepG2 | hepatoblastoma | >15 | >15 |
| R- | IGF-1R negative fibroblasts | >15 | >15 |
| P6 | fibroblasts with overexpressed IGF-1R | 0.03 | 0.02 |

*nd, not determined

Podophyllotoxin and picropodophyllin are very potent inhibitors of tumor cell viability.

Experiment 6. Inhibition of malignant cell growth in vivo

Four to five-week old pathogen-free nude mice (nu/nu) were used and housed within plastic isolators in a sterile facility. The Ewing's sarcoma cell line ES-1 and the melanoma cell line BE (both proved to express IGF-1R) were injected subcutaneously at 10$^7$ cells/mice in a 0.2 ml volume of sterile saline solution. Experimental treatments with podophyllotoxin, deoxypodophyllotoxin or picropodophyllin were performed by daily intraperitoneal injections of the compound in 100 µl volume of solvent, composed of a mixture of DMSO and physiological saline (8:2). Control mice were treated with the solvent. 3-6 animals were treated in each group. Animals were monitored three times a week for signs of disease and tumor growth. Tumor mass was estimated using the formula $(d^2 \times D)/2$, where d and D represent the small and large diameters of the tumor, respectively. The mice were carefully observed for presence of side effects and were sacrificed at the end of the experiments for histological analysis of the lesions. All experiments were performed according to the ethical guidelines for laboratory animal use, provided by institutional ethical committee.

The first set of experiments was carried out to investigate possible local and systemic toxic effects of podophyllotoxin, deoxypodophyllotoxin and picropodophyllin on nude mice. In the first experiment osmotic pumps loaded with either drug-free solvent, podophyllotoxin (0.25 mg), deoxypodophyllotoxin (0.25 mg) or picropodophyllin (0.25 mg) were implanted subcutaneously in the flank region. The drugs are delivered subcutaneously with a constant flow of 0.6 µl/h over 7 days. The volume of the pumps was 100 µl. After 7 days the mice were killed and the skin and subcutaneous tissue adjacent to the outlet of the pumps were analyzed and scored for tissue reactions by an experienced pathologist. There were 3 mice in each group. Treatment with the solvent (control) did not give rise to any damages. In contrast, podophyllotoxin caused severe tissue reactions with necrosis, bleeding and inflammation (Table 5). Mice treated with deoxypodophyllotoxin got light damages, while the picropodophyllin-treated animals exhibited no visible reactions (Table 5).

In the next experiment we analyzed systemic effects of the drugs by injecting 100 µl intraperitoneally of each compound daily over 5 days. Two doses were injected (7 or 28 mg/kg/d) and 3-6 mice were used for each drug and dose. The mice were checked carefully daily for signs of discomfort, diseases and weight loss. It was first confirmed that the mice tolerated the drug-free solvent well. However, mice treated with the low as well as with the high dose of podophyllotoxin became sick and within 2 days 67% and 100%, respectively, of the animals were dead (Table 6). Low-dose deoxypodophyllotoxin-treated mice exhibited serious signs of disease after 3 days. At the high dose the experiment was stopped after 2 days because of serious disease or death. In contrast, mice treated with either dose of picropodophyllin survived the whole 5-day experiments and did not exhibit any evidence of disease (Table 6).

Figure 6A:
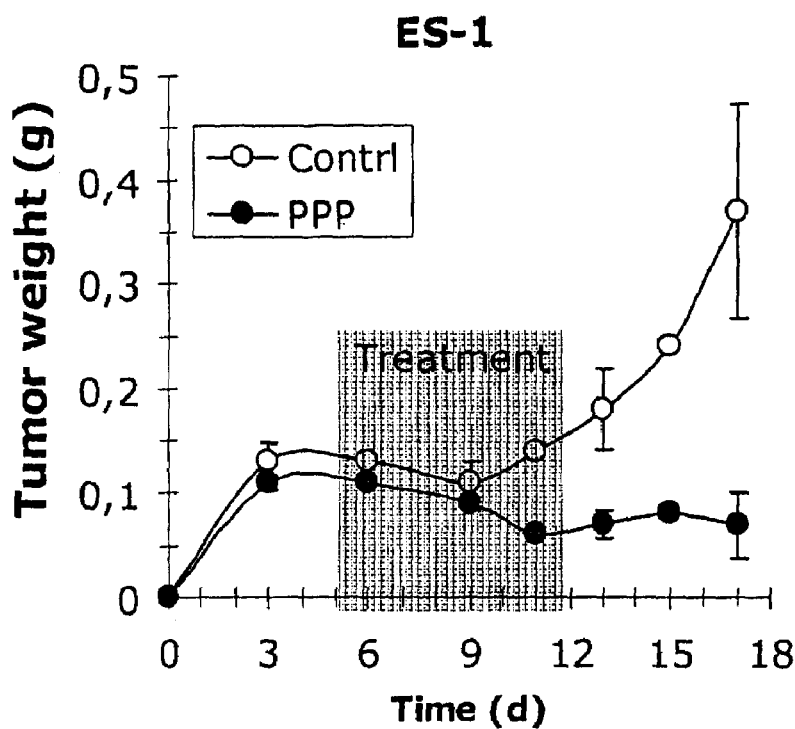
FIGS. 6A and 6B are diagrams showing the effect of picropodophyllin on tumor weight in mice.
Figure 6B:
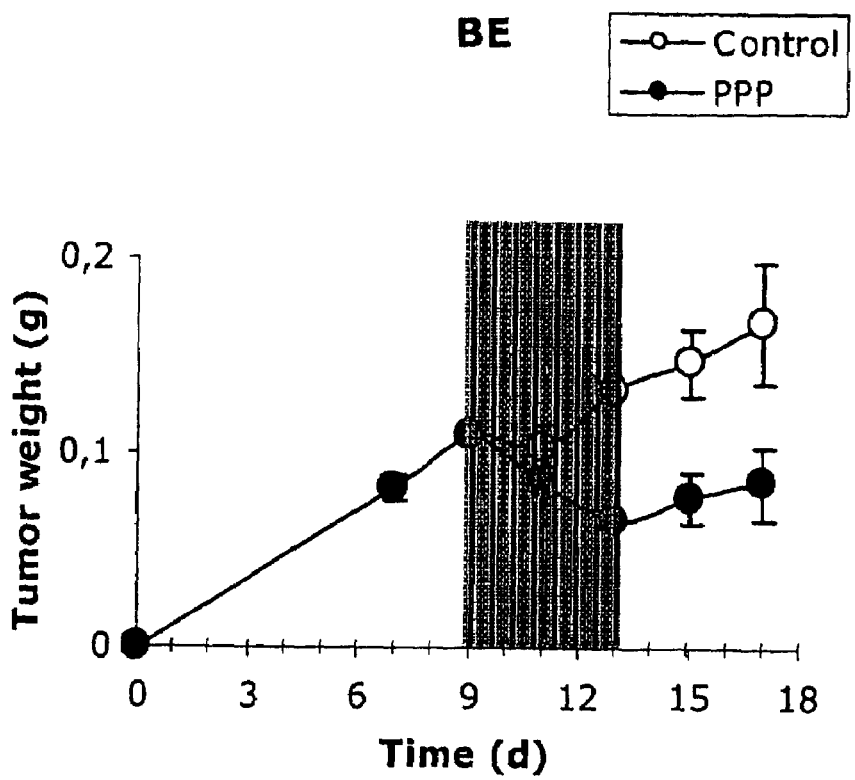

Because of the toxicity of podophyllotoxin and deoxypodophyllotoxin, we only used picropodophyllin to analyze effects on tumor xenografts. For this purpose ES-1 (Ewing's sarcoma cells) and BE (melanoma cells) xenografts were established in nude mice. When the ES-1 and BE tumors started growing subcutaneously and were measurable, mice were treated daily with intraperitoneal injections of picropodophyllin (28 mg/kg, which was required for giving an average concentration above 0.05 µM of picropodophyllin in the blood plasma) or 80% DMSO in saline as a carrier for 4-6 days, followed by 4-6 days without treatment. The mice were then killed and the tumors analyzed by an experienced pathologist. Picropodophyllin significantly inhibited growth of both types of tumors and caused regression (see FIG. 6A and 6B), and the histological analysis of the tumor specimens revealed massive necrosis.

The results show that picropodophyllin, in contrast to podophyllotoxin and deoxypodophyllotoxin, is well tolerated by the animals, and causes tumor regression.

TABLE 5

Local toxicity

| Compound | Effects on skin and subcutaneous tissue* |
|---|---|
| Solvent | 0 |
| Podophyllotoxin (7 mg/kg/d) | +++ |
| Deoxypodophyllotoxin (7 mg/kg/d) | + |
| Picropodophyllin (7 mg/kg/d) | 0 |

0, no tissue reaction; *light tissue reaction with hyperemia and mild inflammation; . moderate tissue reaction with strong inflammation; *, strong tissue reaction with necrosis and bleedings.

TABLE 6

Systemic toxicity

| Compound and dose in mg/kg/d | Surviving mice/Investigated mice | | | | |
|---|---|---|---|---|---|
| | 1 d | 2 d | 3 d | 4 d | 5 d |
| Solvent | 6/6 | 6/6 | 6/6 | 6/6 | 6/6 |
| Podophyllotoxin, 7 mg | 3/3 | 1/3 | 0/3 | — | — |
| Podophyllotoxin, 28 mg | 2/6 | 0/6 | — | — | — |
| Deoxypodophyllotoxin, 7 mg | 3/3 | 3/3 | 3/3 | 3/3 | 3/3 |
| Deoxypodophyllotoxin, 28 mg | 6/6 | 4/6 | 0/6 | — | — |
| Picropodophyllin, 7 mg | 3/3 | 3/3 | 3/3 | 3/3 | 3/3 |
| Picropodophyllin, 28 mg | 6/6 | 6/6 | 6 6 | 6/6 | 6/6 |

Experiment 7. Effects of picropodophyllin and derivatives on survival of human leukemia cells The leukemia cell lines (K562/S, K562/Vcr30, HL60/0 and HL60/Nov) all express the IGF-1R, as assayed by Western blotting analysis, as described in Methods and Experiment 1 and 2.

Cells of said cell lines were seeded in 96-well plates (25 000 cells/well, medium volume per well was 100 μl), in RPMI40 medium supplemented with fetal calf serum. After 24 h picropodophyllin and the derivatives alpha-apopicropodophyllin and beta-apopicropodophyllin were added at different concentrations and the cells were incubated for 72 h. Cell viability was then assayed (see above). EC50 values for each compound and cell line are shown below (Table 7). The results are based on 3 different experiments.

The results, presented in Table 7, show that 0.11-0.32 μM picropodophyllin is needed to cause 50% cell death in 3 of the 4 cell lines, whereas more than 0.5 μM is required for the vincristine-resistant cell line K562/Vcr30. In contrast, the $IC_{50}$ values for alpha- and beta-apopicropodophyllin were as low as 0.01-0.05 μM.

TABLE 7

$IC_{50}$ (μM) for cell viability

| | K562/S | K562/Vcr30 | HL60 | HL60/Nov |
|---|---|---|---|---|
| Picropodophyllin | 0.32 | >0.50 | 0.17 | 0.11 |
| Alpha-apopicro | 0.04 | 0.05 | 0.02 | 0.02 |
| Beta-apopicro | 0.01 | 0.01 | 0.01 | 0.01 |

It can be concluded that the picropodophyllin derivatives alpha- and beta-apopicropodophyllin are highly potent inhibitors of leukemia cell growth and survival.

Experiment 8. Interactive effects of picropodophyllin on malignant cells treated with cytostatica The leukemia cell lines K562/S, K562/Nov, HL60/0 and HL60/Nov were cultured in 96-well plates as described in Experiment 7. After 24 h, the cells were treated for 72 h with different concentrations of the anti-cancer agent vincristine, with and without co-incubation with 0.05 μM picropodophyllin. It was proven that picropodophyllin at this concentration did not cause any detectable cell death in the tumor cells. Cell viability was then assayed. $IC_{50}$ values for each inhibitor and cell line are shown below (Table 8). The results are based on 3 different experiments.

As shown, co-incubation with picropodophyllin decreased $IC_{50}$ values for cell viability in all 4 cell lines.

TABLE 8

$IC_{50}$ (nM) for cell viability

| Cell line | Vincristine ($IC_{50}$, nM) | Picropodophyllin (0.05 μM) + Vincristine ($IC_{50}$, nM) |
|---|---|---|
| K562/S | 1.6 | 0.6 |
| K562/Vcr30 | 5.0 | 0.3 |
| HL60/0 | 0.8 | 0.4 |
| HL60/Nov | 1.2 | 0.8 |

The results show that picropodophyllin sensitises malignant cells for conventional cytostatic agents.

Experiment 9. Effects of picropodophyllin and podophyllotoxin on IGF-1R phosphorylation and cell survival of a human psoriasis model cell line HaCaT cells, which are immortalized human keratinocytes and represent a model cell line for psoriasis, were seeded in 6-cm dishes or in 96-well plates (medium volume in a well was 100 μl), at a concentration of 7,000 cells/cm$^2$ in Dulbecco's Modified Eagle's Medium containing 10 e fetal bovine serum. When the cells reached a concentration of 50,000 cells/cm$^2$, they were incubated with podophyllotoxin or picropodophyllin to a final concentration of 0 or 0.05 μM in the culture medium. Treatment with 0 μM represents untreated controls. After 1 h incubation the cells in the 6-cm dishes were harvested for assay and quantification of IGF-1R phosphorylation as described in Experiment 1. After 48 h incubation the cells cultured in the 96-well plates were assayed for cell viability by means of the Cell proliferation kit II, as described above.

The results show that both podophyllotoxin and picropodophyllin are efficient inhibitors of IGF-1R phosphorylation and cell viability in HaCaT cells.

TABLE 9

Effects of 0.05 μM of podophyllotoxin and picropodophyllin on level of IGF-1R phosphorylation (1 h) and cell survival of HaCaT cells (48 h).

| Compound | IGF-1R phosphorylation | Cell viability |
|---|---|---|
| Control | 100 | 100 |
| Podophyllotoxin | 45 | 30 |
| Picropodophyllin | 35 | 35 |

Experiment 10. Effects of podophyllotoxin and picropodophyllin on IGF-1R phosphorylation and cell proliferation of cultured human vascular smooth muscle cells (VSMC) in a model for artheriosclerosis and restenosis IGF-1 is a growth promoter for arterial cells and a mediator of cardiovascular diseases, such as coronary artheriosclerotic plaque development and restenosis after coronary angioplasty. A key role in these events is played by an excessive growth of VSMC in the vessel wall, which is caused by IGF-1 (Bayes-Genis A, et al., ibid.). For the experiment, the isolated and cultured VSMC are grown in 24-well plates (20.000-40.000 cells/well) and studies on effects of podophyllotoxin and picropodophyllin on IGF-1R phosphorylation and growth and survival of the VSMC are performed essentially as described in Experiment 9. In addition, cell proliferation is assessed by measuring ($^3$H) thymidine incorporation into DNA (DNA synthesis) and ($^3$H)leucine incorporation into (20.000-40.000 cells/well) are grown in 24-well plates and incubated for 24 h with the addition of 1 µCi/ml ($^3$H)thymidine and of IGF-1 (nM-µM concentrations; alone or present in fetal bovine serum) with and without podophyllotoxin or picropodophyllin at different concentrations (0-1.0 µM). The cells are then washed with F12-medium and DNA is precipitated with 5% ice cold trichloroacetic acid(TCA). DNA is solubilized in 0.1 M KOH and 500 µl of the solution in each well is added to scintillation liquid and the radioactivity determined in a liquid scintillation counter. In the latter case, cells are incubated for 24 h as described above, but without ($^3$H) thymidine. Instead ($^3$H)leucine is added to reach a concentration of 1 µCi/ml, but only for the last 90 minutes of the incubation. The cells are then rinsed with cold phosphate buffered saline (pH=7.4) and proteins are precipitated in ice-cold TCA. The proteins are solubilized in a solution containing: 5% sodium dodecyl sulphate, 20 mM $Na_2CO_3$ and 2 mM EDTA. Radioactivity is determined by liquid scintillation counting. The results on DNA and protein synthesis in VSMC are presented as % of control cells, i.e. those incubated without podophyllotoxin or picropodophyllin.

CONCLUSION

It has been demonstrated that picropodophyllin, as well as derivatives thereof having a cis configuration in the lactone ring, are highly specific and potent inhibitors of the IGF-1R tyrosine kinase.

Picropodophyllin-induced inactivation of the insulin-like growth factor-1 receptor caused extensive cell death in malignant cells, whereas cells devoid of insulin-like growth factor-1 receptors were resistant. This new mechanism of picropodophyllin and derivatives thereof may be useful in therapy of cancer and other IGF-1R dependent diseases.

The invention claimed is:
1. A method of treating leukaemia, malignant melanoma, Ewing's sarcoma, breast cancer or prostate cancer, comprising administering to a mammal an effective amount of a compound represented by the formula (I):

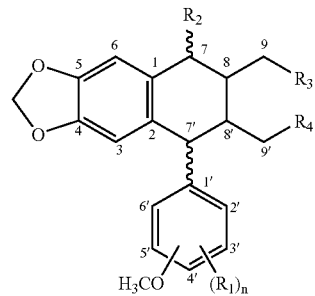

wherein
$R_1$ is $OCH_3$,
n is 0, 1 or 2,
$R_2$ is H or OH, and
$R_3$ and $R_4$ together are an ether or a lactone, and
wherein the carbon atoms at positions 9 and 9' have cis configuration,
with the proviso that when n is 2 and $R_2$ is H, $R_3$ and $R_4$ together are an ether.

2. The method of claim 1, wherein the compound represented by formula I is administered in the form of composition which also comprises a physiologically acceptable diluent.

3. The method of claim 1, wherein the compound is administered for the treatment of malignant melanoma, Ewing's sarcoma, breast cancer or prostate cancer.

4. The method of claim 1, wherein the compound is administered for the treatment of leukemia.

5. The method of claim 1, wherein the compound inhibits the insulin-like growth factor-1 receptor without inhibiting the insulin receptor.

6. The method of claim 1, wherein the compound is picropodophyllin.

7. The method of claim 1, wherein the compound is administered in an amount effective for keeping the plasma level of the compound at a concentration of 0.05-5.0 µM.

8. The method of claim 1, wherein the compound of formula I is administered with a cytostaticum.

9. The method of claim 1, wherein the compound is administered for the treatment of malignant melanoma.

10. The method of claim 1, wherein the compound is administered for the treatment of Ewing's sarcoma.

11. The method of claim 1, wherein the compound is administered for the treatment of breast cancer.

12. The method of claim 1, wherein the compound is administered for the treatment of prostate cancer.

* * * * *